United States Patent [19]

Riffle

[11] Patent Number: 5,733,538
[45] Date of Patent: Mar. 31, 1998

[54] SURFACE-MODIFYING COPOLYMERS HAVING CELL ADHESION PROPERTIES

[75] Inventor: Judy S. Riffle, Blacksburg, Va.

[73] Assignee: Thoratec Laboratories, Inc., Berkeley, Calif.

[21] Appl. No.: 487,604

[22] Filed: Jun. 7, 1995

[51] Int. Cl.[6] ............. A61K 31/74; A61K 31/745; A61K 31/785; A61K 38/00; A61K 38/03; A61K 38/04; C08H 5/00; C08L 25/06; C08L 25/08; C08L 75/04; C08L 75/12; C08L 83/04; C08G 77/388; C07K 4/00; C07K 5/00; C07K 7/00; C07K 17/08

[52] U.S. Cl. ................. 424/78.08; 424/78.17; 424/78.18; 424/78.27; 424/78.31; 424/78.35; 424/78.37; 514/2; 524/17; 524/20; 524/188; 524/261; 524/262; 524/265; 524/267; 524/269; 524/498; 524/499; 524/506; 524/507; 524/515; 524/577; 524/588; 524/589; 524/590; 525/541; 525/54.11; 525/88; 525/90; 525/92 R; 525/92 A; 525/92 C; 525/92 G; 525/96; 525/95; 525/100; 525/101; 525/102; 525/106; 525/123; 525/130; 525/217; 525/231; 525/241; 525/452; 525/453; 525/455; 525/457; 526/238.1; 526/279; 526/346; 528/10; 528/44; 528/25; 528/28; 528/85; 527/200; 527/201; 527/203; 527/204; 530/300; 530/345

[58] Field of Search ............... 424/78.08, 78.17, 424/78.18, 78.27, 78.31, 78.35, 78.37; 514/2; 525/54.1, 54.11, 100, 101, 88, 102, 106, 90, 217, 231, 92 R, 241, 123, 92 A, 130, 452, 92 C, 453, 455, 92 G, 96, 95, 457; 530/300, 345; 524/17, 20, 188, 261, 262, 265, 267, 269, 498, 499, 506, 507, 515, 577, 588, 589, 590; 528/10, 44, 25, 28, 85; 526/238.1, 279, 346; 527/200, 201, 203, 204

[56] References Cited

U.S. PATENT DOCUMENTS

| | | | |
|---|---|---|---|
| 4,689,383 | 8/1987 | Riffle et al. | 528/12 |
| 4,789,601 | 12/1988 | Banes | 428/447 |
| 4,822,741 | 4/1989 | Banes | 435/300 |
| 4,839,280 | 6/1989 | Banes | 435/285 |
| 5,324,591 | 6/1994 | Georger, Jr. et al. | 428/552 |
| 5,330,911 | 7/1994 | Hubbell et al. | 435/240.23 |
| 5,369,012 | 11/1994 | Koontz et al. | 435/180 |
| 5,510,628 | 4/1996 | Georger, Jr. et al. | 257/32 |

OTHER PUBLICATIONS

J.A. Hubbell et al., *Endothelial Cell–Selective Materials for Tissue Engineering in the Vascular Graft Via a New Receptor*, Bio./TEchnology, 9:568–571 (1991).

J.A. Hubbell et al., *Surface–grafted Cell–binding Peptides in Tissue Engineering of the Vascular Graft*, Annals of the NY Academy of Sciences, 665:253–258 (1992).

*Primary Examiner*—Rabon Sergent
*Attorney, Agent, or Firm*—Fish and Richardson P.C.

[57] ABSTRACT

A hemocompatible surface-modifying additive is provided for modifying polyurethane or polyurethane urea substrates. The additive has a polyurethane or polyurethane urea hard block or an alternative block which is miscible with the poly(urethane) or poly(urethane-urea) base polymer, a polysiloxane hydrophobic soft block, an optional hydrophilic spacer and a peptide selected from the group consisting of Arg-Gly-Asp, X-Arg-Gly-Asp, Arg-Gly-Asp-X and X-Arg-Gly-Asp-X', wherein X and X' are amino acids.

11 Claims, No Drawings

SURFACE-MODIFYING COPOLYMERS HAVING CELL ADHESION PROPERTIES

FIELD OF THE INVENTION

The present invention is directed to novel block copolymers which are hemocompatible surface-modifying additives for modifying polyurethane, poly (urethane urea), polystyrene or polystyrene-containing elastomer substrates.

BACKGROUND OF THE INVENTION

Cell adhesion to natural or synthetic substrates is mediated by the interaction of cell adhesion proteins which correspondingly accommodate cell surface receptors. Cell adhesion proteins are exemplified by fibronectin, vibronectin, collagen, thrombospondin, von Willebrand factor and laminin, all found in the extracellular matrix. These cell adhesion proteins have cell surface receptors having varying specificity depending on the particular receptor. In many cases the cell binding sequences within the cell adhesion proteins which comprise part of the receptor consist of variants of the sequence RGDX (where X is a variant amino acid) (RGDX equals Arg-Gly-Asp-X). For example, RGDS is one of the sequences found in fibronectin, fibrinogen and von Willebrand factor which aids adhesion to cells. Fibronectin also contains RGDX-like adhesion sequences such as REDV (Arg-Glu-Asp-Val). Since the sequences within the cell adhesion proteins appear to be responsible for cell adhesion, there have been studies of the binding capacity of these particular short sequences when they are not within the context of the larger protein. For example, J. A. Hubbell et al., Bio/Technology, 1991, 9, 568–571, and Annals of the NY Academy of Sciences, 665, 1992, 253–258, disclosed a study of cell and blood platelet binding activity onto surfaces with covalently attached RGD amino acid sequences. These sequences supported the spreading and growth of human fibroblasts, human vascular smooth muscle cells and human umbilical cord endothelial cells, but did not support the spreading of blood platelets. Sequences containing REDV attached in the same manner specifically supported the spreading and growth of human umbilical cord endothelial cells but also did not support the spreading of blood platelets.

Accordingly, there is a need to develop synthetic biomaterials for applications in the human cardiovascular system which will resist blood coagulation by promoting the growth of protective endothelial layers over the surfaces but yet which would also mediate the buildup of thrombus. Biomaterial surfaces comprising either hydrophilic (e.g., polyethylene oxide) or extremely hydrophobic (e.g., polydimethylsiloxane) are known in medical devices and are the subject of ongoing investigation for such cardiovascular applications, but such biomaterials are not as thromboresistant as endothelialized surfaces. Thus while it is currently possible to produce devices for relatively short-term functions while using anticoagulants to aid in preventing clotting, there are no suitable materials for lifetime applications.

The present invention provides nonpolar polydimethylsiloxane blocks incorporated into a block copolymer onto which is covalently linked a particular chemical sequence for increased cell adhesion. The nonpolar polydimethylsiloxane blocks selectively segregate toward the air interface of the substrate polymer surface as a result of the thermodynamic driving force to minimize surface free energy. The cell adhesion sequence covalently linked thereto will also be pulled toward the surface of the polymer films by virtue of the fact that they are covalently bound to the polydimethylsiloxane. The copolymers can either be blended with substrate polymers in low amounts, coated onto substrate polymers in low amounts, or covalently attached to the substrate polymers. When placed in contact with blood, the cell adhesion amino acid sequences will rise to the surface in the hydrophilic environment, and selectively bind endothelial cells and will not bind blood platelets. Thus endothelial tissue unique to the individual in which the device is implanted will grow over the biomaterial surface and blood will not coagulate on this surface. Since only the surface of the biomaterial will expose the polydimethylsiloxane-amino acid copolymers, a variety of bulk polymeric substrates may be used which have a wide range of mechanical and morphological properties.

SUMMARY OF THE INVENTION

The copolymers of the present invention will comprise at least three blocks or segments, each with a specific function, that is, an anchor block, a surface active block and the amino acid sequence. There may be an optional short hydrophilic spacer between the hydrophobic polydimethylsiloxane surface active block and the amino acid sequence. The function of the anchor block will be to provide the ability to form a film so that the copolymer will not be extracted from the biomaterial surface in the presence of blood, and to provide compatibility with the bulk material. This is an important feature in view of regulatory concerns. The anchor block must be chemically compatible with the bulk of the biomaterial substrate. For example, copolymers with polystyrene anchor blocks will be suitable for blending with or coating onto polystyrene, polystyrene containing elastomers, or polyphenylene oxide. Copolymers containing either polyurethane or polyurea segments would be suitable for blending with polyurethane, polyurea, or poly(urethane-urea) bulk materials. Alternatively, a short, hydrophilic, spacer such as poly(2-ethyloxazoline) or poly(ethylene oxide) can be inserted between the polydimethylsiloxane and the amino acid sequence.

BRIEF DESCRIPTION OF THE DRAWING

DESCRIPTION OF THE PREFERRED EMBODIMENTS

The copolymers provided in accordance with the present invention comprise at least three blocks or segments. By the term block it is meant that there is one type of recurring unit. Although the term block is a generic term, the term "segment" is sometimes used in the art to represent a relatively short length of repeating units, e.g., less than about ten monomeric units, but preferably less than 3 monomeric units, typically alternating more than once with structural formulas such as ABAB. Block copolymers or segmented copolymers are composed of at least two blocks, one block composed of one type of recurring unit and at least one other block composed of a different type of recurring unit. Block copolymers as defined herein may be linear, cyclic or branched (cross-linked) structures. The preferred block copolymers in accordance with the present invention are linear.

The block copolymers according to the present invention are hemo-compatible surface-modifying copolymer additives having the formulas:

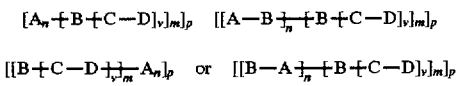

wherein A is a poly(urethane), poly(urethane-urea), or polystyrene hard block; B is a polysiloxane hydrophobic softblock; C is an optional hydrophilic spacer; and D is peptide sequence selected from the group consisting of: Arg-Gly-Asp, X-Arg-Gly-Asp, Arg-Gly-Asp-X and X'-Arg-Gly-Asp-X wherein X and X' are any amino acid; and each n, v, m, and p is independently an integer greater than 0 up to about 500. Each n, v, m, and p is preferably independently an integer greater than 0 up to about 100. The preferred amino acid for X and X' is Gly.

Copolymers containing the anchor block and the surface-active block can be made in a variety of ways. For example, if the anchor block is polystyrene an activated terminus polystyrene may be prepared and then reacted with a cyclic siloxane to produce a copolymer of the anchor block (polystyrene) and the surface active block (polysiloxane). The copolymer can then be reacted with an amino acid sequence.

An exemplary scheme is shown below. In scheme 1 sec-butyl-lithium is reacted with styrene to produce an alkyl lithium terminated polystyrene. This in turn is reacted with cyclic polysiloxane then capped with a silane having an activated terminal (in this case, chloromethyl) for further reaction.

The hard block (A) need not be a poly(urethane) or poly(urethane urea), as long as it is a hard block which is thermodynamically miscible with a poly(urethane), or poly (urethane urea) base polymer. Likewise, the hard block need not be a polystyrene, as long as it is a hard block which is miscible with a polystyrene or polystyrene-containing base polymer.

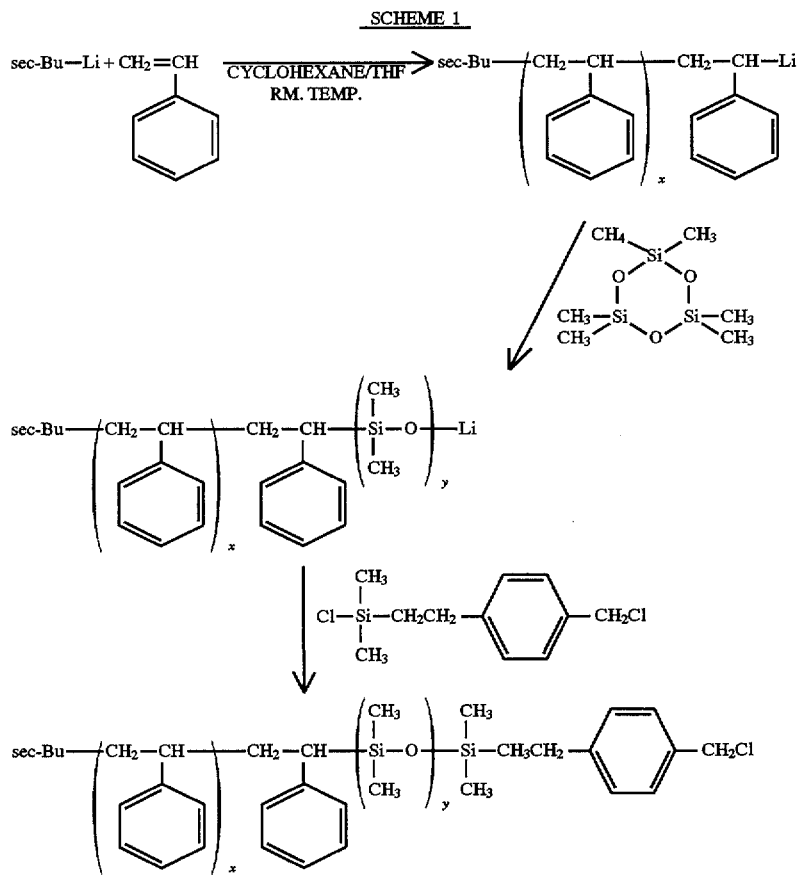

Scheme 1: Preparation of Poly(styrene-co-dimethylsiloxane)

In scheme 2 the terminal chloromethyl group is converted to an iodomethyl group then treated with the peptide.

SCHEME 2

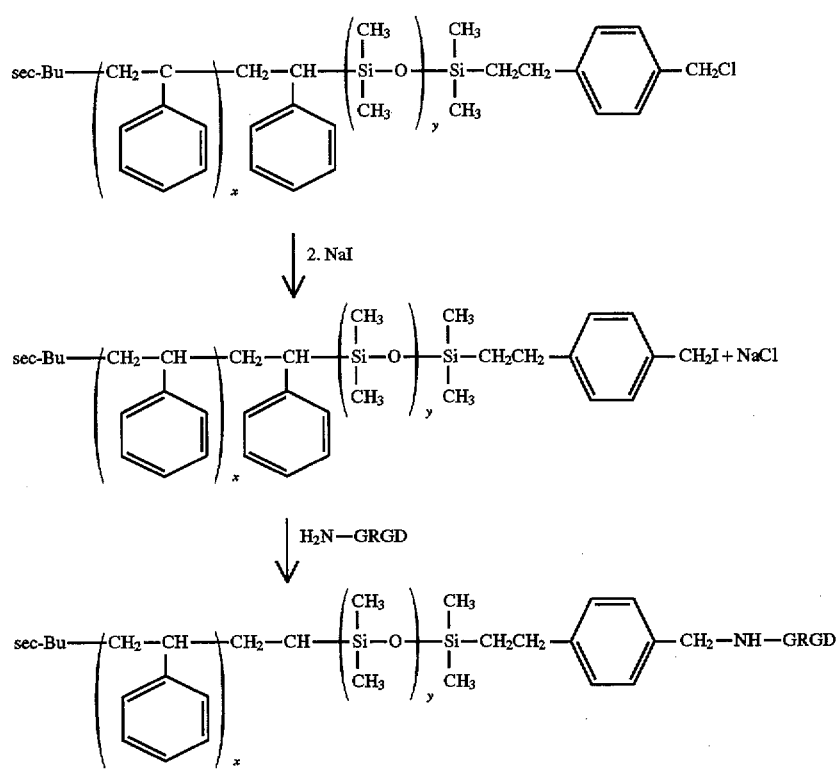

GRGD = gly — arg — gly — asp

Scheme 2: Preparation of Poly(styrene-co-dimethylsiloxane-co-amino acid sequence)

Alternatively, the polystyrene polysiloxane copolymer can be end-capped with activated ethyloxazoline groups for reaction with the peptide. Referring below to scheme 3, the methylene chloride-terminated polystyrene polysiloxane copolymer is treated with ethyloxazoline to make the ethyloxazoline-terminated intermediates, which after treatment with the peptide GRGD, results in the peptide-terminated copolymer.

SCHEME 3

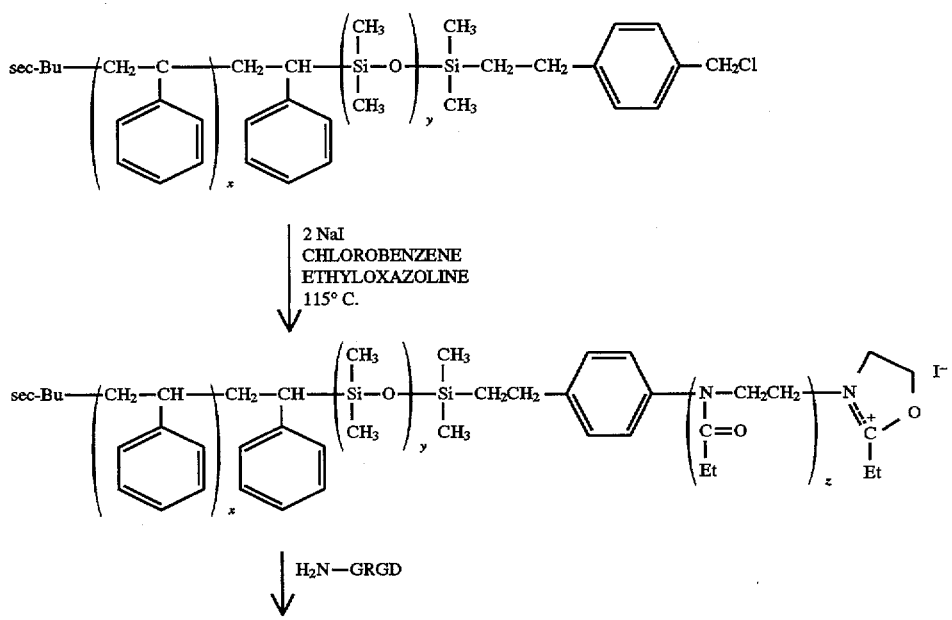

-continued
SCHEME 3

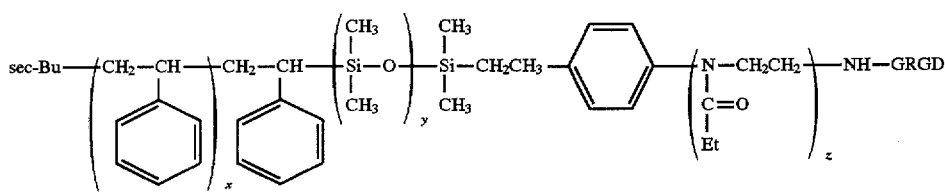

Scheme 3: Preparation of Poly(styrene-co-dimethylsiloxane-co-ethyloxazoline-co-amino acid sequence)

Alternatively, hydroxy functional dimethylsiloxane end-blocking reagents may be prepared whereby the molecular weight of polydimethylsiloxane oligomers can be controlled by synthetic conditions. Thus polysiloxane-urethane blocked polymers may be prepared modified with appended peptide moieties (such as RGD) which are covalently linked to the polysiloxane portion of the chain via an arginine N-terminal.

A preferred group of hydroxy-terminated oligomeric precursors is described below in scheme 4. (See U.S. Pat. No. 4,689,383 to J. S. Riffle & R. S. Ward, 1987.)

loxanes having functional substituents such as cyanopropyl in addition to methyl attached to the silicon atoms can be polymerized with the $D_4$ to prepare analogous siloxane oligomers with pendent functional groups along the oligomer backbone. The yield of the desired polymer is sensitive to the size of the substituent group on the silicon atoms in the siloxane system whereby the yield decreases for hydrogen, alkyl groups, and trifluoromethylpropyl as the substituents increase in size. However, a cyanopropyl-methylcyclotetrasiloxane yields a high volume fraction of polymer (about 75% when equilibrated with trifluoromethanesulfonic acid catalyst).

A polyurethane copolymer backbone with pendent benzyl butyrate substituents may be synthesized in a manner similar

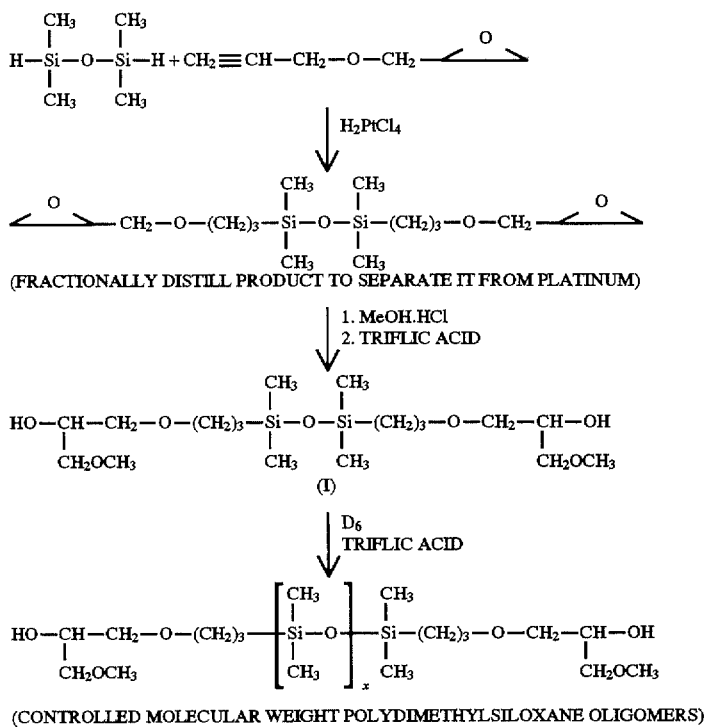

(CONTROLLED MOLECULAR WEIGHT POLYDIMETHYLSILOXANE OLIGOMERS)

Scheme 4: Preparation of hydroxyfunctional dimethylsiloxane endblocking reagent (I), and controlled molecular weight polydimethylsiloxane oligomers with hydroxyl endgroups.

A polydimethylsiloxane is reacted with an epoxy allyl ether to form the epoxy-terminated siloxane. The epoxy end groups are then opened with methanol and then coequilibration is used to create oligomers of desired molecular weight ranges using D4, a cyclosiloxane tetramer. Cyclosito the methods used for preparing block copolymers. Polysiloxane prepolymers may be end-capped by reaction with an excess of methylene diphenyldiisocyanate and then extended with 1,4-butanediol. The benzyl esters may be removed by known methods, such as by hydrogenation. This is shown in scheme 5, below.

SCHEME 5
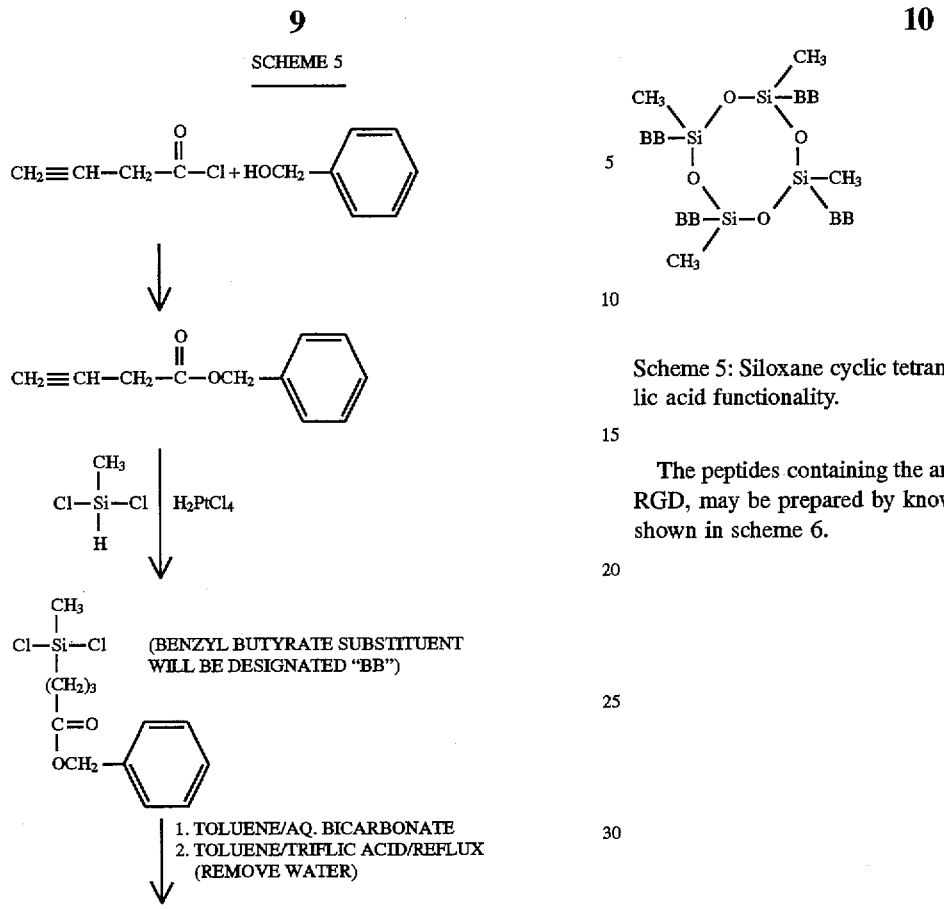
Scheme 5: Siloxane cyclic tetramer with protected carboxylic acid functionality.
The peptides containing the amino acid segments such as RGD, may be prepared by known procedures such as that shown in scheme 6.
SCHEME 6
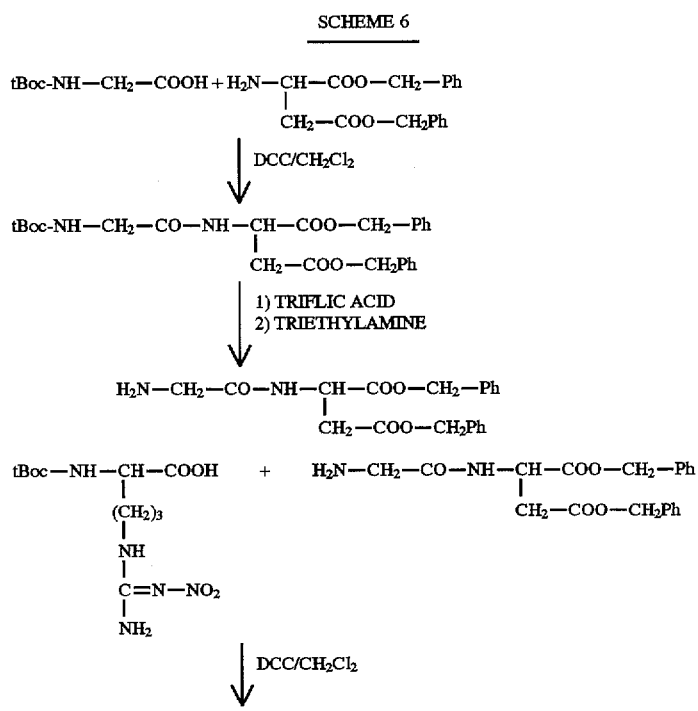

-continued
SCHEME 6

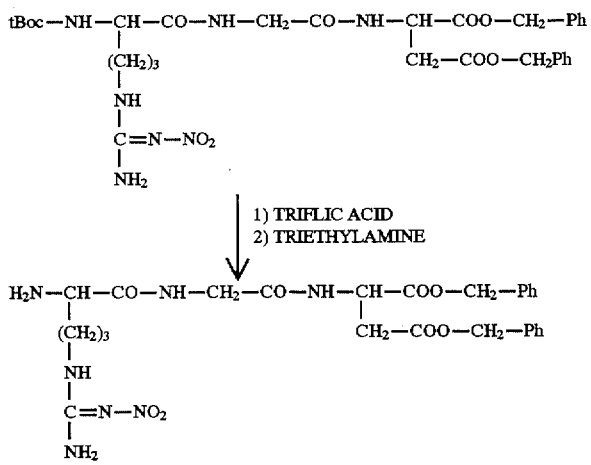

Scheme 6: RGD segment preparation.

The amine terminus of these graft segments may be deblocked and the grafts bonded to the pendent carboxypropyl units on a block copolymer using dicyclohexyl carbodiimide as an activating agent as shown in scheme 7.

reactions conducted in the presence of the acid liable siloxane bonds may be achieved using hydrogenation, as opposed to acid hydrolysis, to ensure that the copolymer backbone remains unaffected.

SCHEME 7

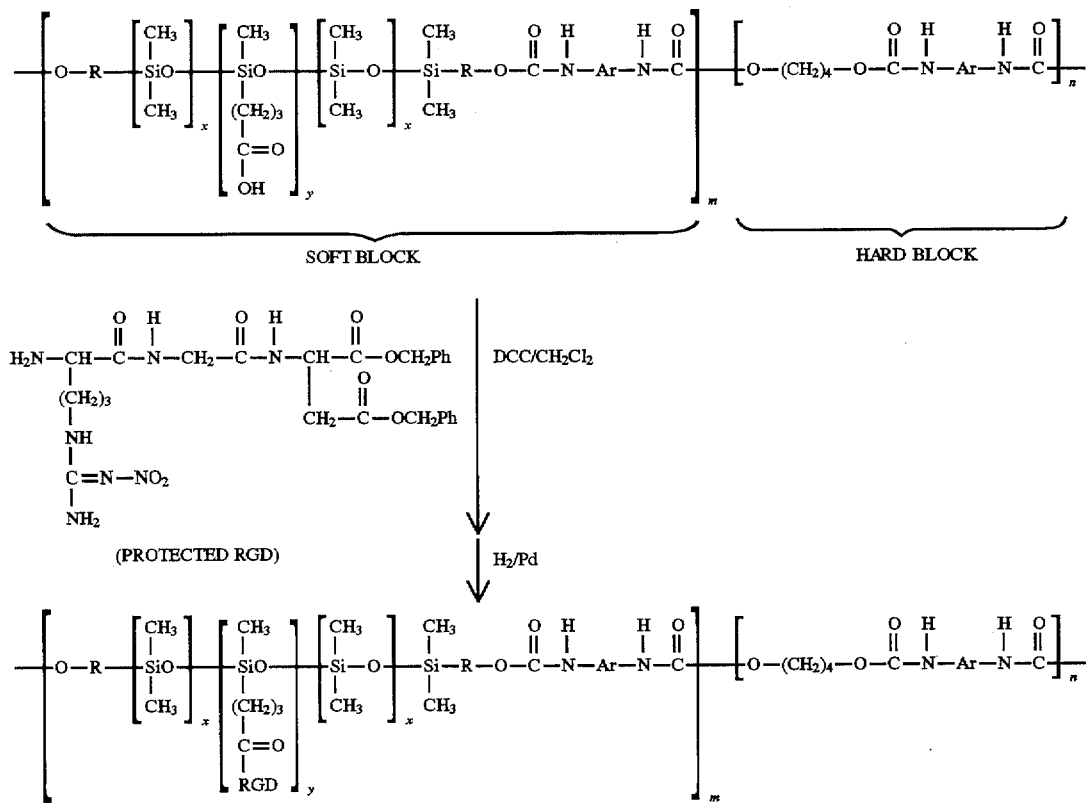

Scheme 7: Attachment to RGD segments to the polymer backbone.

The remaining benzyl ester protecting groups on the aspartic acid may be deprotected by hydrogenation. Deprotection As an alternative to the last step in scheme 4, the following process (shown in scheme 8) may be utilized to prepare hydroxy-functional polysiloxane oligomers with pendent protected carboxy groups.

SCHEME 8

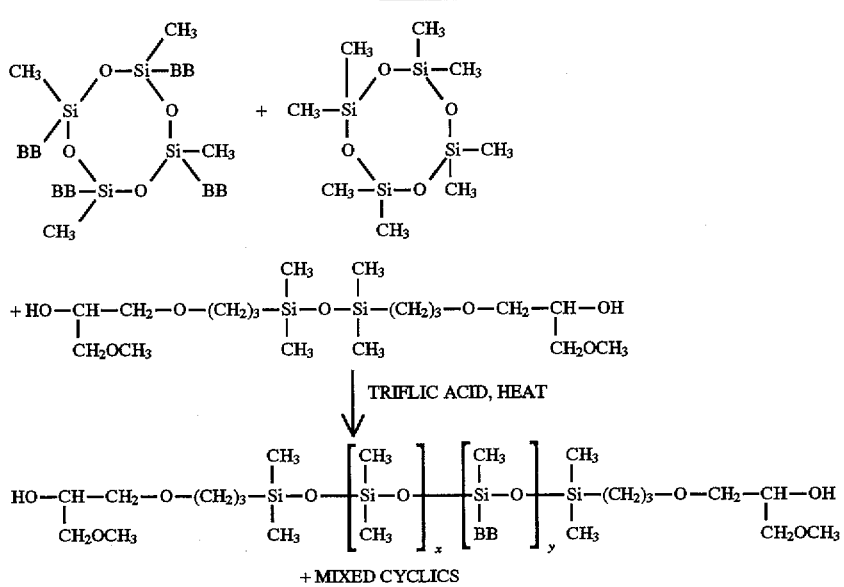

Scheme 8: Preparation of hydroxy functional polysiloxane oligomers with pendant protected carboxy groups. Due to the mechanism of equilibration reactions, the sequence of "x" and "y" units will be randomly distributed along the chain. The sequences of the repeat units indicated with subscripts x and y are randomly distributed along the chain. Polyethylene oxide spacers can be added to the amine terminal of the arginine residue via the method outlined in schemes 9 and 11 using protein synthesis techniques (Merrifield method) to produce—PEO-RGD pendent groups.

SCHEME 9

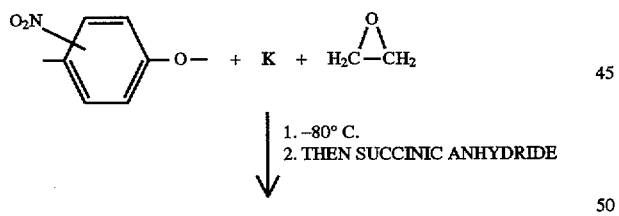

-continued
SCHEME 9

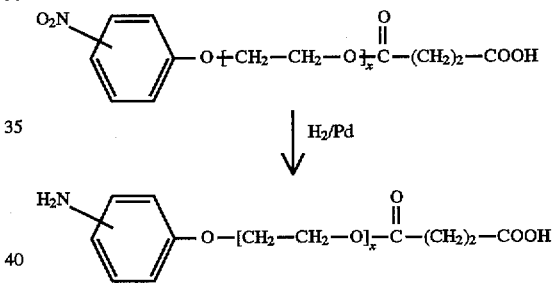

Scheme 9: Preparation of polyethylene oxide spacers with an amine terminus and with a carboxylic acid terminus. The starting material is preferably the p-nitro-phenoxide salt.

SCHEME 11

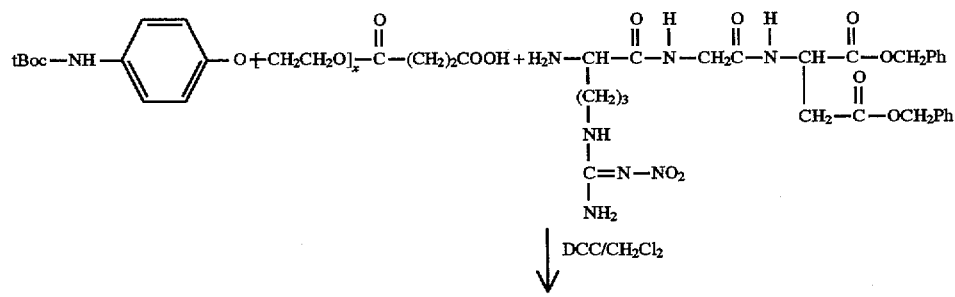

-continued
SCHEME 11

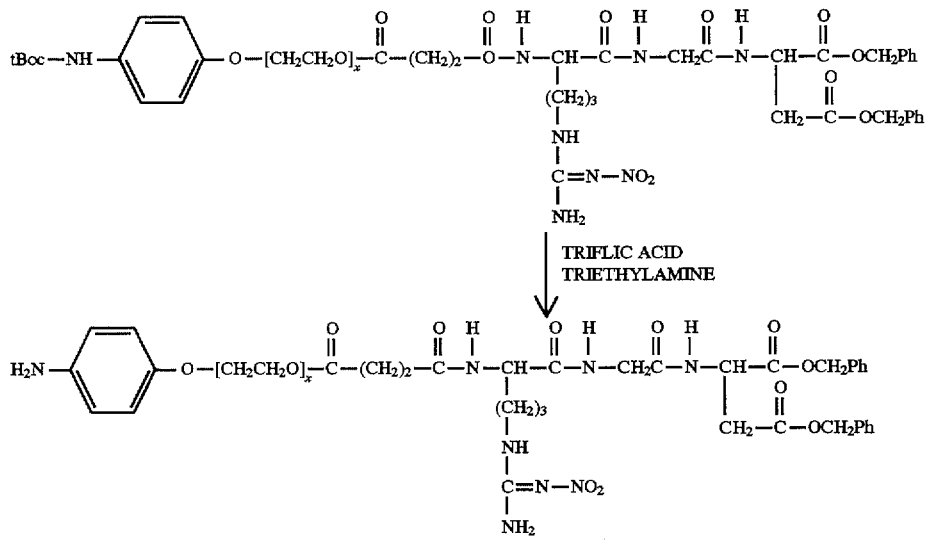

Scheme 11: Preparation of RGD segments with hydrophilic PEO spacer units.

This oligomeric group may be appended to the carboxyl group on the siloxane portion of the copolymer by coupling the amine terminus to the PEO unit as shown in scheme 10.

Scheme 10: Polysiloxane-urethane block copolymers containing pendent amino acids appended via hydrophilic spacers.

It will be realized that other types of spacers may be utilized such as poly(alkyloxazoline), polyacrylamides,

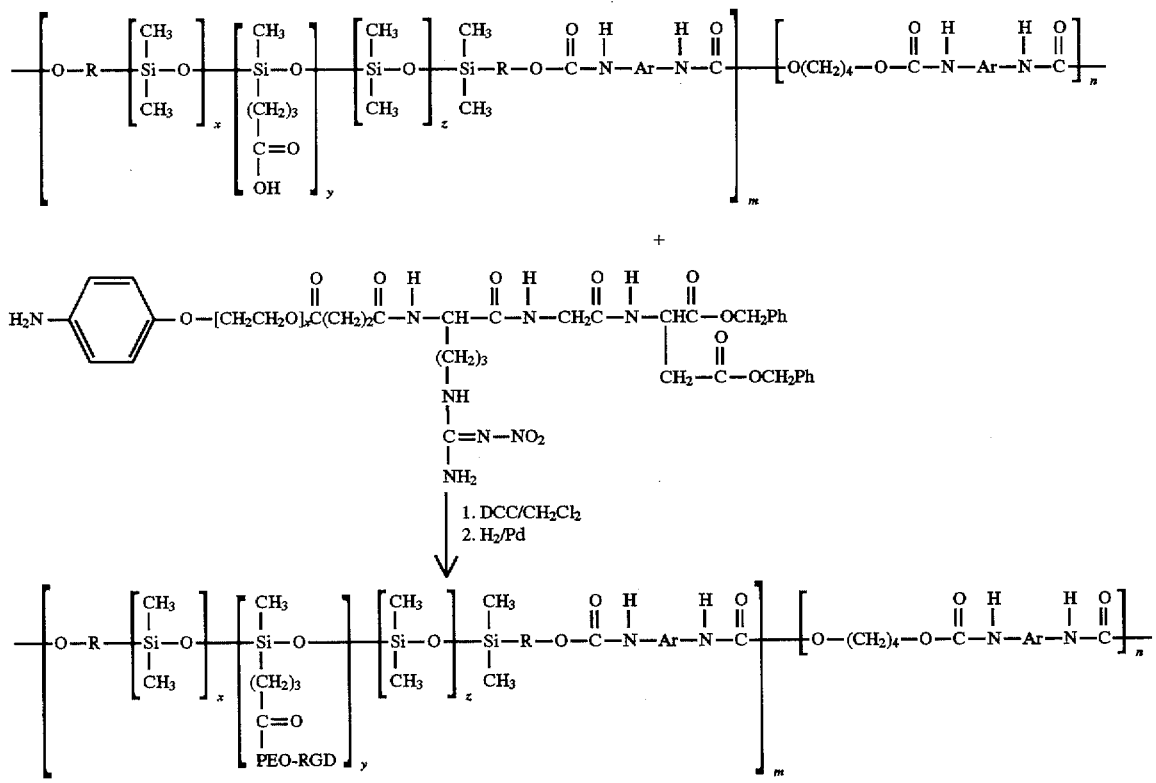

polylvinylpyrrolidone). However, the polyethylene oxide spacers or other polyalkylene oxide spacers are preferred since the binding strength to hydrogen bonding surfaces of ether oxygens is expected to be less than the binding strength of the amino bonds of the amino acid segments. Therefore, the polyethylene oxide spacers would not substantially interfere with the binding process of the amino acids to the cell surfaces.

Referring to Scheme 5, vinylacetic acid can either be coupled directly to benzylalcohol using known activating agents (e.g. dicyclohexylcarbodiimide), or it can first be converted to the corresponding acid chloride and subsequently esterified to form benzyl vinylacetate, and then is reacted with dichloromethylsilane to produce benzyl butyrate silane. This is then converted to the cyclic siloxane tetramer having protected carboxylic acid functionalities. Referring to Scheme 8, this siloxane tetramer can then be equilibrated with D4 and siloxane hydroxy terminated monomers to form the hydroxy functional terminated polysiloxane oligomers with pendent protected carboxy groups. Referring to Scheme 6 there is shown a conventional Merrifield synthesis scheme for coupling amino acids to make the peptide RGD. Referring to Scheme 9 there is shown the preparation of polyethylene oxide spacers having an amine terminus and a carboxylic acid terminus. Referring to Scheme 7 there is shown the addition of the protected peptides to the carboxy terminal pendant groups of hydroxy functional polysiloxane oligomers and then removal of the protecting groups to form, in this case, a polyurethane polysiloxane polymer backbone having pendent RGD groups. Referring to Scheme 11 there is shown the attachment of the PEO spacers to the amino terminus of the RGD end of the RGD peptide.

It will be realized that other linear polymers may be utilized such as polysiloxane-polylactone block copolymers, examples of which are described in U.S. Pat. No. 4,663,413 incorporated herein by reference. Methods of preparation of dihydroxy functional polydimethylsiloxane oligomers are further disclosed in U.S. Pat. No. 4,689,383, incorporated herein by reference.

The polymers according to the present invention are useful for surface modification of base polymers which are poly(urethane), poly(urethane-urea)s, polystyrenes or polystyrene-containing elastomers, to allow endothelial cell adhesion thereto, thereby forming endothelial monolayers which are nonthrombogenic. Typically, the polymers according to the present invention may be utilized as additives to the poly(urethane), poly(urethane-urea), polystyrene, or polystyrene-containing elastomer base polymer in amounts of 0.1 to 20 percent by weight. The base polymer modified according to the present invention may be used in blood-contacting devices, such as vascular prostheses in the venous or arterial system, heart patches, heart valves, as the outer encapsulants of implantable devices such as pacemakers, catheters or the outer sheath of catheters in contact with body fluids, temporary coverings on open wounds. The surface may also be utilized in extracorporeal devices to provide channels through which body fluids may be passed in heart, lung and kidney machines.

What is claimed is:

1. A hemocompatible surface-modifying copolymer additive for modifying poly(urethane), poly(urethane urea) or polystyrene base polymers, said additive having the formulas $$[A_n-\!\!+\!\!B-\!\!+\!\!C-\!\!D]_v]_m]_p \quad [[A-\!\!B\tfrac{1}{n}\!\!+\!\!B-\!\!+\!\!C-\!\!D]_v]_m]_p$$

$$[[B-\!\!+\!\!C-\!\!D\tfrac{1}{v}\tfrac{1}{m}A_n]_p \quad \text{or} \quad [[B-\!\!A\tfrac{1}{n}\!\!+\!\!B-\!\!+\!\!C-\!\!D]_v]_m]_p$$

wherein A is a polyurethane, poly(urethane urea) or polystyrene hard block; B is a polysiloxane hydrophobic soft block; C is an optional hydrophilic spacer; D is a peptide selected from the group consisting of the sequence -Arg-Gly-Asp, -X-Arg-Gly-Asp, Arg-Gly-Asp-X and -X-Arg-Gly-Asp-X', wherein X and X' are any amino acid; and n, v, m and p are each independently an integer greater than 0 up to about 500.

2. An additive according to claim 1 wherein X is Gly.

3. An additive according to claim 1 wherein said spacer is a polyalkylene oxide.

4. An additive according to claim 1 wherein said additive is of the formula $$[A_n-\!\!+\!\!B-\!\!+\!\!C-\!\!D]_v]_m]_p.$$

5. An additive according to claim 1 wherein said additive is of the formula $$[[B-\!\!+\!\!C-\!\!D\tfrac{1}{v}\tfrac{1}{m}A_n]_p.$$

6. An additive according to claim 1 wherein said additive is of the formula $$[[A-\!\!B\tfrac{1}{n}\!\!+\!\!B-\!\!+\!\!C-\!\!D]_v]_m]_p.$$

7. An additive according to claim 1 wherein said additive is of the formula $$[[B-\!\!A\tfrac{1}{n}\!\!+\!\!B-\!\!+\!\!C-\!\!D]_v]_m]_p.$$

8. A copolymer additive according to claim 1 wherein n, v, m, and p are each independently an integer greater than 0 up to 100.

9. A blood-contacting device comprising a blood-contacting surface of a base polymer and an additive according to claim 1 of the formula:

$$[A_n-\!\!+\!\!B-\!\!+\!\!C-\!\!D]_v]_m]_p \quad [[A-\!\!B\tfrac{1}{n}\!\!+\!\!B-\!\!+\!\!C-\!\!D]_v]_m]_p$$

$$[[B-\!\!+\!\!C-\!\!D\tfrac{1}{v}\tfrac{1}{m}A_n]_p \quad \text{or} \quad [[B-\!\!A\tfrac{1}{n}\!\!+\!\!B-\!\!+\!\!C-\!\!D]_v]_m]_p$$

or mixtures of two or more different additives of said formulas.

10. A method of modifying a poly(urethane) substrate to impart a hemocompatible surface thereto, comprising the step of incorporating into said substrate an effective hemocompatible surface-active amount of an additive according to any one of claims 1 through 7.

11. A method of modifying a poly(urethane urea) substrate to impart a hemocompatible surface thereto, comprising the step of incorporating into said substrate an effective hemocompatible surface-active amount of an additive according to any one of claims 1 through 7.

* * * * *